(12) United States Patent
Abe et al.

(10) Patent No.: US 9,888,892 B2
(45) Date of Patent: Feb. 13, 2018

(54) X-RAY DIAGNOSTIC IMAGING APPARATUS

(71) Applicant: TOSHIBA MEDICAL SYSTEMS CORPORATION, Otawara-Shi (JP)

(72) Inventors: Shingo Abe, Nasushiobara (JP); Satoru Ohishi, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 112 days.

(21) Appl. No.: 14/883,949

(22) Filed: Oct. 15, 2015

(65) Prior Publication Data
US 2016/0113608 A1 Apr. 28, 2016

(30) Foreign Application Priority Data
Oct. 22, 2014 (JP) .................................. 2014-215285

(51) Int. Cl.
*A61B 6/00* (2006.01)

(52) U.S. Cl.
CPC ............. *A61B 6/466* (2013.01); *A61B 6/504* (2013.01); *A61B 6/5211* (2013.01); *A61B 6/4441* (2013.01); *A61B 6/4464* (2013.01)

(58) Field of Classification Search
CPC ...................................................... A61B 6/542
See application file for complete search history.

(56) References Cited

U.S. PATENT DOCUMENTS 8,611,499 B2  12/2013  Spahn
8,681,941 B2   3/2014  Bernhardt et al.

FOREIGN PATENT DOCUMENTS

JP    2000-152924    6/2000
JP    2013-078635    5/2013

*Primary Examiner* — Dani Fox
(74) *Attorney, Agent, or Firm* — Oblon, McClelland, Maier & Neustadt, L.L.P.

(57) ABSTRACT

An X-ray diagnostic imaging apparatus according to this embodiment includes a display for displaying an image and a processing circuitry which calculates an incident dose on a body surface of an object, superposes information based on the calculated incident dose on a three-dimensional image which is a three-dimensional image relating to the object and is capable of rotating display at a corresponding position on the body surface of the object and causes the three-dimensional image on which the information is superposed to be displayed on the display.

20 Claims, 10 Drawing Sheets

X-RAY DIAGNOSTIC IMAGING APPARATUS

CROSS-REFERENCE TO RELATED APPLICATION

This application is based upon and claims the benefit of priority from Japanese Patent Application No. 2014-215285, filed on Oct. 22, 2014, the entire contents of which are incorporated herein by reference.

FIELD

An embodiment of the present invention relates to an X-ray diagnostic imaging apparatus.

BACKGROUND

A prior-art X-ray diagnostic imaging apparatus irradiates an X-ray from outside a human body, catches the X-ray transmitted through the human body by an X-ray detector and observes a contrast image in proportion to a transmitted radiation. Thus, in a radiotherapy using an X-ray diagnostic imaging apparatus or an X-ray irradiating apparatus, an irradiation dose to an object has been a problem.

Various measures have been taken to reduce the irradiation dose of the X-ray recently, and reduction of the irradiation dose by the X-ray and grasping of skin incident dose to the object are in demand.

In relation with the X-ray diagnostic imaging apparatus relating to an X-ray circulatory organ diagnostic system, for example, an X-ray diagnostic imaging apparatus displaying the skin incident dose to the object during X-ray photography using a human body model is proposed.

Here, when the X-ray is irradiated to the object, an operator can visually recognize the fact that the skin incident dose increases by having the skin incident dose displayed on the human body model.

If the skin incident dose increases during irradiation of the X-ray to the object, a portion irradiated with the X-ray is preferably changed in order to suppress disorder caused by the X-ray irradiation. In this case, in the X-ray diagnostic imaging apparatus, the portion to be irradiated is changed by changing a position of an arm supporting an apparatus for irradiating an X-ray and a detector for detecting the X-ray.

However, even if the skin incident dose is displayed on the human body model and the position of the arm is changed on the basis of the skin incident dose, the changed position of the arm does not necessarily match manipulation, and determination of an appropriate arm position has been difficult.

Thus, an X-ray diagnostic imaging apparatus capable of easily determining a working angle indicating an appropriate position of the arm considering the skin incident dose has been in demand.

DETAILED DESCRIPTION

An X-ray diagnostic imaging apparatus according to this embodiment includes a display for displaying an image and a processing circuitry for calculating an incident dose on a body surface of an object, superposing information based on the calculated incident dose on a three-dimensional image which is a three-dimensional image relating to the object and is capable of rotating display at a corresponding position on the body surface of the object and causing the three-dimensional image on which the information is superposed to be displayed on the display.

First Embodiment

An embodiment of an X-ray diagnostic imaging apparatus according to a first embodiment will be described below by referring to the attached drawings.

Figure 1:
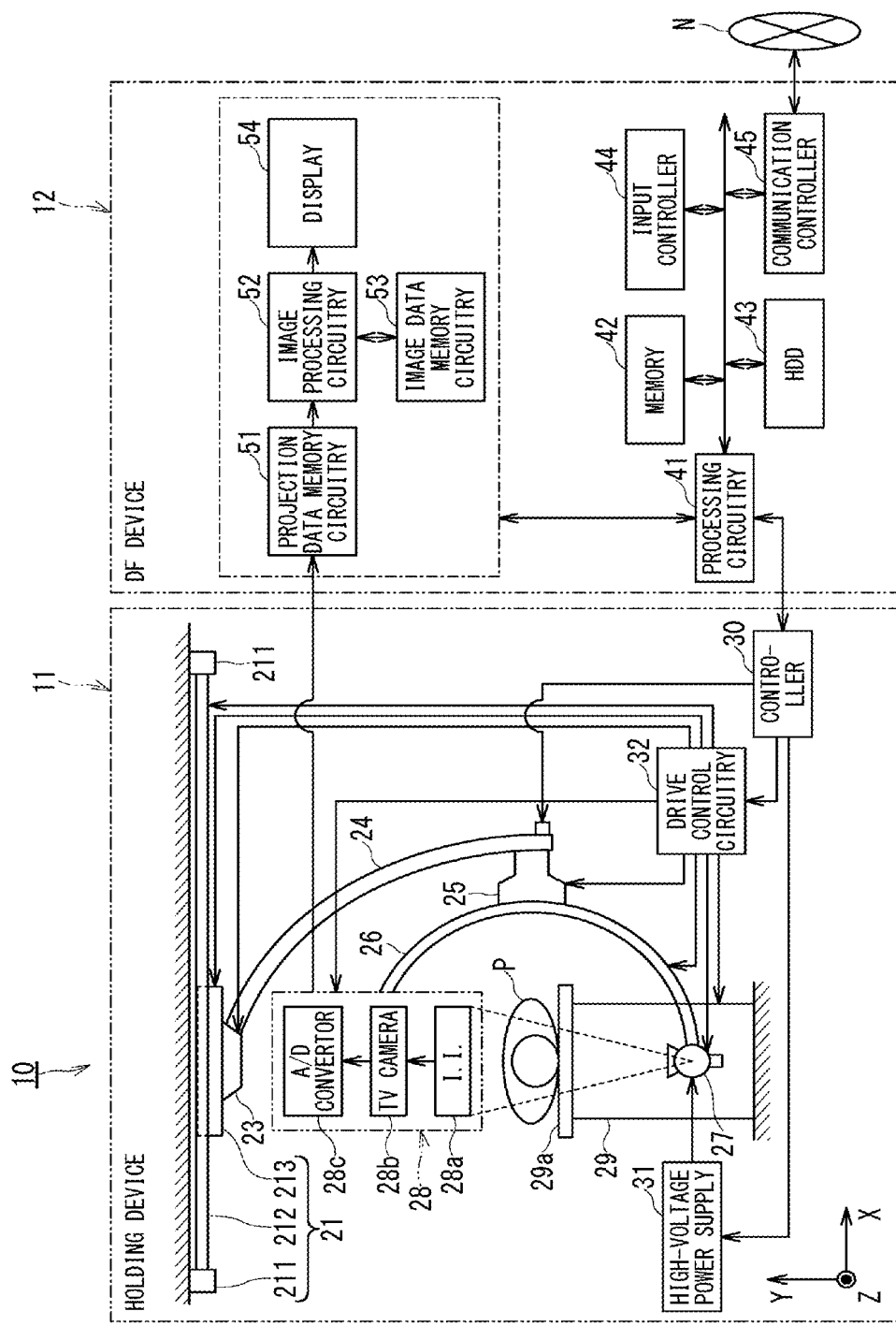
FIG. 1 is an outline diagram illustrating hardware configuration of an X-ray diagnostic imaging apparatus of a first embodiment.
Figure 2:
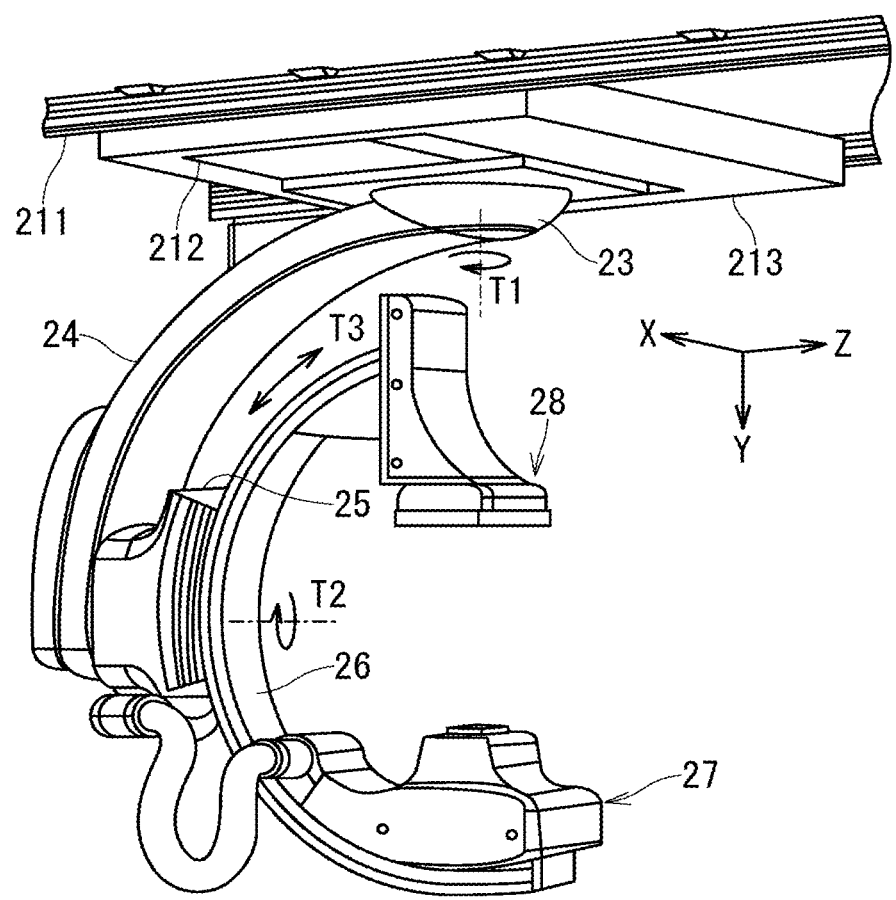
FIG. 2 is a perspective view illustrating appearance configuration of a holding device in the X-ray diagnostic imaging apparatus of the first embodiment.

FIG. 1 is an outline view illustrating hardware configuration of an X-ray diagnostic imaging apparatus 10 of the first embodiment. FIG. 2 is a perspective view illustrating appearance configuration of a holding device 11 in the X-ray diagnostic imaging apparatus 10 of the first embodiment.

In FIG. 1, an X-ray diagnostic imaging apparatus 10 provided with a ceiling-traveling type C-arm of the first embodiment is illustrated. The X-ray diagnostic imaging apparatus 10 is constituted by the holding device 11 and a DF (Digital Fluorography) device 12. The holding device 11 and the DF device 12 are installed in an examination room or a treatment room in general.

The X-ray diagnostic imaging apparatus 10 according to the first embodiment is not limited to the X-ray diagnostic imaging apparatus provided with the ceiling-traveling type C-arm but may be an X-ray diagnostic imaging apparatus provided with a floor-traveling type C-arm or may be an X-ray diagnostic imaging apparatus provided with a floor installation type C-arm. Moreover, the X-ray diagnostic imaging apparatus provided with the C-arm will be described as an example of the X-ray diagnostic imaging apparatus according to the first embodiment, but this is not limiting. For example, an X-ray irradiating device and an X-ray detector may be held by respective independent arms or the X-ray diagnostic imaging apparatus may be such that the C-arm is not used.

The holding device 11 includes a slide mechanism 21, a vertical axis rotating mechanism 23, a suspended arm 24, a C-arm rotating mechanism 25, a C-arm 26, an X-ray irradiating device 27, a detector 28, a bed 29, a controller 30, a high-voltage power supply 31, and a drive control circuitry 32.

The slide mechanism 21 includes a Z-axis direction rail 211, an X-axis direction rail 212, and a truck 213. The slide mechanism 21 slides the vertical axis rotating mechanism 23, the suspended arm 24, the C-arm rotating mechanism 25, the C-arm 26, the X-ray irradiating device 27, and the detector 28 integrally in a horizontal direction by control of the controller 30 through the drive control circuitry 32.

The Z-axis direction rail 211 is extended in the Z-axis direction (a long axis direction of a top plate 29a) and is supported on a ceiling.

The X-axis direction rail 212 is extended in the X-axis direction (a short axis direction of the top plate 29a) and is supported by the Z-axis direction rail 211 through rollers (not shown) on both ends thereof. The X-axis direction rail 212 is moved in the Z-axis direction on the Z-axis direction rail 211 by control of the controller 30 through the drive control circuitry 32.

The truck 213 is supported by the X-axis direction rail 212 through rollers (not shown). The truck 213 moves in the X-axis direction on the X-axis direction rail 212 by control of the controller 30 through the drive control circuitry 32.

The X-axis direction rail 212 supporting the truck 213 is movable in the Z-axis direction on the Z-axis direction rail 211, and the truck 213 is movable in the X-axis direction on the X-axis direction rail 212 and thus, the truck 213 is movable in the horizontal direction (X-axis direction and Z-axis direction) in the examination room.

The vertical axis rotating mechanism 23 is rotatably supported by the truck 213. The vertical axis rotating mechanism 23 rotates the suspended arm 24, the C-arm rotating mechanism 25, the C-arm 26, the X-ray irradiating device 27, and the detector 28 integrally in a vertical axis rotating direction T1 (illustrated in FIG. 2) by control of the controller 30 through the drive control circuitry 32.

The suspended arm 24 is supported by the vertical axis rotating mechanism 23.

The C-arm rotating mechanism 25 is rotatably supported by the suspended arm 24. The C-arm rotating mechanism 25 rotates the C-arm 26, the X-ray irradiating device 27, and the detector 28 integrally in a rotating direction T2 (illustrated in FIG. 2) with respect to the suspended arm 24 by control of the controller 30 through the drive control circuitry 32.

The C-arm 26 is supported by the C-arm rotating mechanism 25 and arranges the X-ray irradiating device 27 and the detector 28 faced with each other with respect to an object P at a center. A rail (not shown) is provided on a rear surface or a side surface of the C-arm 26, and the C-arm 26 moves the X-ray irradiating device 27 and the detector 28 integrally in an arc direction T3 (illustrated in FIG. 2) of the C-arm 26 through the rail sandwiched by the C-arm rotating mechanism 25 and the C-arm 26 by control of the controller 30 through the drive control circuitry 32.

The X-ray irradiating device 27 is provided on one end of the C-arm 26. The X-ray irradiating device 27 is provided capable of moving forward/backward by control of the controller 30 through the drive control circuitry 32. The X-ray irradiating device 27 has an X-ray tube and irradiates an X-ray toward a predetermined portion of the object P in accordance with a condition of high-voltage power upon receipt of supply of the high-voltage power from the high-voltage power supply 31. The X-ray irradiating device 27 includes an X-ray irradiation field aperture constituted by a plurality of lead blades, a compensation filter formed of silicon rubber or the like and damping a predetermined amount of an irradiated X-ray in order to prevent halation or the like on an outgoing side of the X-ray. The X-ray irradiating device 27 adjusts the X-ray irradiation field aperture and specifies a position of interest of the object P when the X-ray is irradiated to the object P on the basis of irradiation information on irradiation of the X-ray.

The detector 28 is provided on another side of the C-arm 26 and on the outgoing side of the X-ray irradiating device 27. The detector 28 is provided capable of moving forward/backward by control of the controller 30 through the drive control circuitry 32. The detector 28 is an I.I. (Image Intensifier)—TV system and includes an I.I. 28a, a TV camera 28b, and an A/D (Analog to Digital) convertor 28c. The I.I. 28a coverts the X-ray transmitted through the object P and the direct incident X-ray to visible light and moreover, it forms projection data with good sensitivity by doubling brightness in a process of light-electron-light conversion. The TV camera 28b converts optical projection data to an electric signal by using a CCD (Charge Coupled Device) image pickup device. The A/D convertor 28c converts a time-series analog signal (video signal) output from the TV camera 28b to a digital signal.

The detector 28 may include an FPD (Flat Panel Detector). If the detector 28 includes the FPD, the detector 28 detects the X-ray by detection devices arrayed in a 2D manner and converts it to the electric signal. As described above, it is only necessary that the detector 28 can detect the X-ray transmitted through the object P or the directly incident X-ray.

The bed 29 is supported by a floor surface and supports a top plate (catheter table) 29a. The bed 29 moves the top plate 29a horizontally (X- and Z-axis directions) and vertically (Y-axis direction) and rolls it by control of the controller 30 through the drive control circuitry 32. The top plate 29a can have the object P placed thereon and is movable. The holding device 11 of an under-tube type in which the X-ray irradiating device 27 is located below the top plate 29a is described, but it may be of an over-tube type in which the X-ray irradiating device 27 is located above the top plate 29a, or the bed 29 may be constituted so as to drive the top plate 29a by the X-ray diagnostic imaging apparatus not having the C-arm.

The controller 30 includes a CPU (Central Processing Unit), not shown, and a memory. The controller 30 controls operations of the high-voltage power supply 31, the drive control circuitry 32 and the like. The controller 30 controls the drive control circuitry 32 driving the bed 29 and the top plate 29a and the like and thus, positional information of the bed 29 indicating a position of the bed 29 and positional information of the top plate 29a indicating a position of the top plate 29a can be calculated.

The high-voltage power supply 31 can supply high-voltage power to the X-ray irradiating device 27 in accordance with control of the controller 30.

The drive control circuitry 32 can drive the slide mechanism 21, the vertical axis rotating mechanism 23, the C-arm rotating mechanism 25, the C-arm 26, the X-ray irradiating device 27, the detector 28, and the top plate 29a of the bed 29, respectively, in accordance with control of the controller 30.

The DF device 12 is constituted on the basis of a computer and is capable of mutual communication with a network N such as a base LAN (Local Area Network) of a hospital. The DF device 12 is constituted by hardware such as a processing circuitry 41 as a processor, a memory 42, an HDD (Hard Disc Drive) 43, an input controller 44, a communication controller 45, a projection data memory circuitry 51, an image processing circuitry 52, an image data memory circuitry 53, a display 54 and the like. The processing circuitry 41 is mutually connected to each of the hardware constituent elements constituting the DF device 12 via a bus as a common signal transmission path. The DF device 12 is provided with a drive for a recording medium (not shown) in some cases.

The processing circuitry 41 executes a program stored in the memory 42 when an instruction is input by operation of the input controller 44 by an operator such as a doctor, an examination engineer or the like. Alternatively, the processing circuitry 41 loads a program stored in the HDD 43, a program transferred from the network N, received by the communication controller 45, and installed in the HDD 43, and a program read out of a recording medium attached to a drive (not shown) for a recording medium and installed in the HDD 43 into the memory 42 and executes it.

The memory 42 is a memory device having constitution of combining elements such as a ROM (Read Only Memory), a RAM (Random Access Memory) and the like. The memory 42 stores data of IPL (Initial Program Loading) and BIOS (Basic Input/Output System) and is used for temporary storage of work memory or data of the processing circuitry 41.

The HDD 43 is a memory device having constitution in which a metal HD (Hard Disk) which a magnetic body is applied to or deposited on is built in, unable of being removed. The HDD 43 stores a program installed in the DF device 12 (in addition to an application program, OS (Operating System) and the like are also included) and data. Moreover, the HDD 43 can also cause the OS to provide a GUI (Graphical User Interface) capable of executing basic operations using the input controller 44 by frequently using graphics for display of the information to an examination operator.

The input controller 44 includes a keyboard, a mouse and the like capable of an operation by an operator, and an input signal according to the operation is sent to the processing circuitry 41. The input controller 44 is constituted by a main console and a system console.

The communication controller 45 executes communication control in compliance with each standard. The communication controller 45 has a function capable of being connected to the network N via a telephone line or an exclusive line, for example. The DF device 12 can be connected to the network N network via the communication controller 45.

The projection data memory circuitry 51 stores projection data output from the A/D convertor 28c of the holding device 11 by control of the processing circuitry 41.

The image processing circuitry 52 creates data of a transparent image and a photographed image (DA (Digital Angiography) image) from the projection data stored in the projection data memory circuitry 51 by control of the processing circuitry 41. Moreover, the image processing circuitry 52 executes image processing to the transparent image and the photographed image stored in the image data memory circuitry 53. The image processing includes enlargement/gradation/spatial filter processing to the data, minimum value/maximum value trace processing of data accumulated in a time series, addition processing for removing a noise and the like. The data after the image processing by the image processing circuitry 52 is output to the display 54 and is stored in a memory circuitry such as the image data memory circuitry 53 or the like.

The image data memory circuitry 53 stores the transparent image and the photographed image output from the image processing circuitry 52 as data by control of the processing circuitry 41. The image data memory circuitry 53 stores the transparent image and the photographed image (so-called original image) before execution of the image processing, and when it displays an image on the display 54, required image processing is executed every time in the image processing circuitry 52.

The display 54 has a function of displaying an image. For example, the display 54 synthesizes examination information such as a patient name and the like (parameter character information, a scale and the like) with the data of the transparent image and the photographed image created by the image processing circuitry 52 by control of the processing circuitry 41, D/A (Digital to Analog) converts a synthetic signal and then, displays it as a video signal. The display 54 includes a live monitor for live display of the transparent image and the photographed image output from the image processing circuitry 52, a reference monitor for displaying a still image or for replaying and displaying a video of the photographed image output from the image processing circuitry 52, a system monitor for displaying data for executing control mainly of the holding device 11 such as data for switching FOV (Field of View) and the like.

Figure 3:
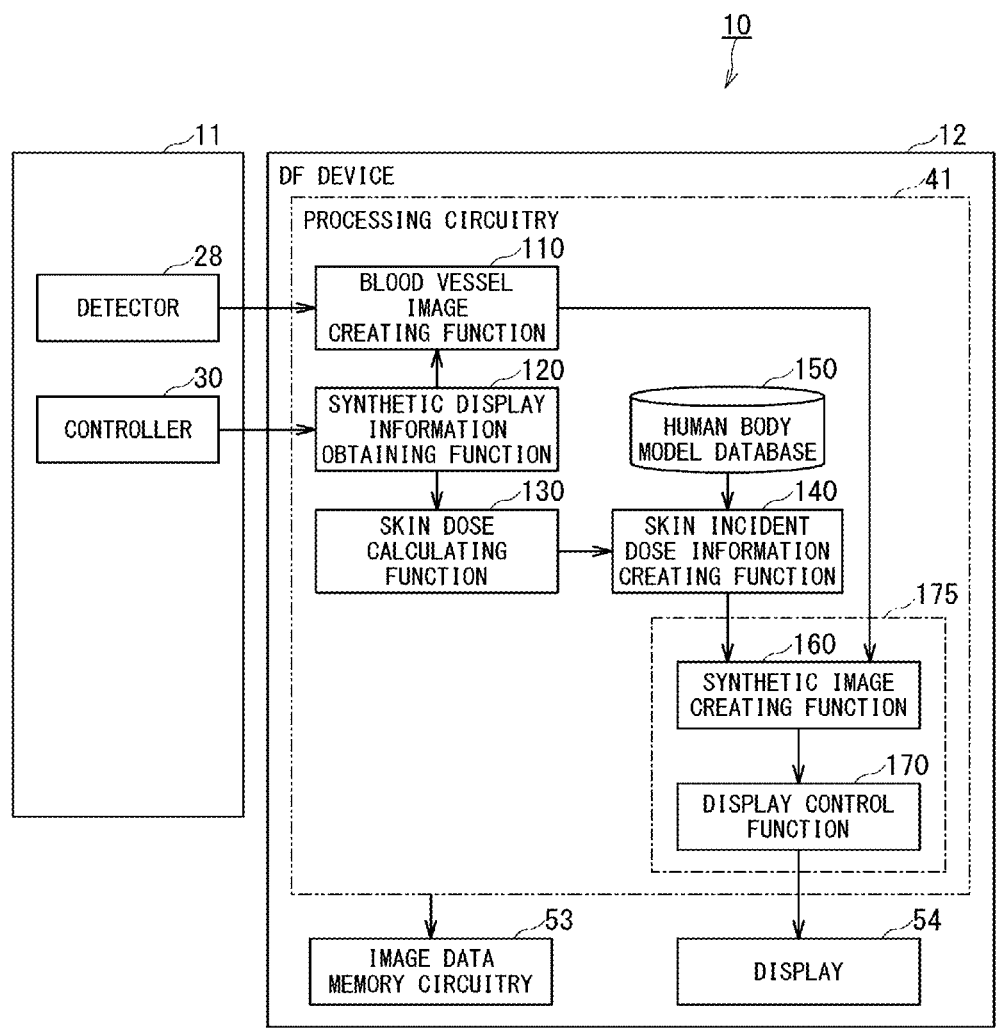
FIG. 3 is a block diagram illustrating functions of the X-ray diagnostic imaging apparatus of the first embodiment.

FIG. 3 is a block diagram illustrating a function of the X-ray diagnostic imaging apparatus 10 of the first embodiment.

As illustrated in FIG. 3, by means of execution of the program by the processing circuitry 41 illustrated in FIG. 1, the DF device 12 has a blood vessel image creating function 110, a synthetic display information obtaining function 120, a skin dose calculating function 130, a skin incident dose information creating function 140, a human body model database 150, a synthetic image creating function 160, and a display control function 170.

That is, the processing circuitry 41 can realize the blood vessel image creating function 110 to the display control function 170 by reading out the corresponding program from the memory 42 or the HDD 43 and by executing it. Moreover, the synthetic image creating function 160 and the display control function 170 constitute the synthetic image display function 175.

The blood vessel image creating function 110 to the display control function 170 will be described to be provided in the DF device 12 as the functions of the X-ray diagnostic imaging apparatus 10, but the whole or a part of the blood vessel image creating function 110 to the display control function 170 may be provided as hardware in the X-ray diagnostic imaging apparatus 10. Moreover, the image data memory circuitry 53 and the display 54 are provided as hardware in the DF device 12 of the X-ray diagnostic imaging apparatus 10 but may be provided as hardware in the diagnostic imaging apparatus 10.

The blood vessel image creating function 110 is a function of creating three-dimensional data (first three-dimensional data) showing an inside of a body of the object P for forming a three-dimensional image obtained by photographing the object P. For example, the blood vessel image creating function 110 obtains the projection data from the detector 28 (or the projection data memory circuitry 51) of the holding device 11 and creates the three-dimensional data for forming a blood vessel image of the object P (hereinafter referred to also as 3D blood vessel image data). The blood vessel image creating function 110 causes the created 3D blood vessel image data to be stored by the image data memory circuitry 53. The blood vessel image is an example and a three-dimensional image obtained by photographing the object P is not limited to the blood vessel image. That is, in this embodiment, the image may be other than the blood vessel image.

Moreover, the blood vessel image creating function 110 creates photographed image data at photographing from the projection data at rotating photographing and may also create the 3D blood vessel image data or may create the 3D blood vessel image data from image data photographed in advance. Moreover, the blood vessel image creating function 110 may obtain the image data or 3D blood vessel image data photographed in another modality (photographing device) and use the obtained image data. The 3D blood vessel image data is assumed to be displayed as the 3D blood vessel image on the display 54. The 3D blood vessel image data created by the blood vessel image creating function 110 is an example and it may be any three-dimensional data which can be displayed as a three-dimensional image. Hereinafter the 3D blood vessel image data is exemplified and described.

The synthetic display information obtaining function 120 is a function of obtaining system information required for synthetic display from the controller 30 and supplying the system information to the blood vessel image creating function 110 or the skin incident dose calculating function 130 when an input for synthesizing the 3D blood vessel image and information based on a skin incident dose is received from the input controller 44. The system information includes an angle of the C-arm 26, a focal distance between image receivers (SID: Source Image Distance), an FOV, a position and a height of the top plate 29a, information relating to the patient, an operation state or setting information relating to the skin incident dose or the like.

The skin incident dose calculating function 130 is a function of calculating a skin incident dose on a body surface of the object P. The skin incident dose calculating function 130 can calculate the skin incident dose on the body surface of the object P. For example, the skin dose calculating function 130 obtains the angle of the C-arm 26, the SID, the information relating to the object P, the X-ray irradiation information and the like by the synthetic display information obtaining function 120 and calculates an exposure dose or an exposure region of the object P during an operation.

The skin incident dose information creating function 140 is a function of creating information based on the skin incident dose to the object P from the skin incident dose calculated by the skin dose calculating function 130. For example, the skin incident dose information creating function 140 creates three-dimensional data (second three-dimensional data) showing information based on the skin incident dose at a body surface position of a human body model showing the object P.

The skin incident dose information creating function 140 obtains the human body model showing physical characteristics of the object P from the human body model database 150 and creates the three-dimensional data showing the skin incident dose information in which an exposure amount and an exposure region are calculated (hereinafter referred to also as 3D skin dose data) at the body surface position of the human body model. The skin incident dose information creating function 140 causes the created 3D skin dose data to be stored in the image data memory circuitry 53.

In this embodiment, since the skin incident dose information creating function 140 can create the 3D skin dose data, the second three-dimensional data is created as three-dimensional data showing information based on the skin incident dose in the three-dimensional data based on the position on the body surface. In the following description, the 3D skin dose data at the body surface position is used for description, but this is not limiting, and the 3D skin dose data may be created at a position of the 3D blood vessel image (coordinate of the 3D blood vessel image data), for example.

The human body model database 150 is a database storing human body models showing physical characteristics of various objects. The human body models stored in the human body model database 150 are selected on the basis of information relating to the object P obtained by the synthetic display information obtaining function 120.

The synthetic image display function 175 is a function of causing information based on the calculated skin incident dose to be superposed on the three-dimensional image of the object P and to be displayed on the display 54. For example, the synthetic image display function 175 causes the 3D skin dose data (second three-dimensional data) showing the skin incident dose information to be superposed on the 3D blood vessel image data (first three-dimensional data) obtained by photographing the object P and to be displayed on the display 54. As described above, the synthetic image display function 175 causes a synthetic image obtained by subjecting the 3D skin dose data to superposing-display on the 3D blood vessel image data to be displayed on the display 54 by the synthetic image creating function 160 and the display control function 170.

Moreover, if the 3D blood vessel image is being rotated, the synthetic image display function 175 highlights the 3D blood vessel image, while if the 3D blood vessel image is not being rotated (stopped), the synthetic image display function 175 highlights the information shown by the 3D skin dose data.

The synthetic image creating function 160 is a function of aligning the 3D blood vessel image data (first three-dimensional data) and the 3D skin dose data (second three-dimensional data) and then, superposing and creating the synthetic image data. For example, the synthetic image creating function 160 obtains the 3D blood vessel image data from the blood vessel image creating function 110 and also obtains the 3D skin dose data from the skin incident dose information creating function 140. The synthetic image creating function 160 synthesizes the 3D blood vessel image data and the 3D skin dose data so as to create the synthetic image data and then, causes the synthetic image data to be stored in the image data memory circuitry 53. The synthetic image creating function 160 may obtain the 3D blood vessel image data and the 3D skin dose data from the image data memory circuitry 53.

The display control function 170 is a function of causing the created synthetic image data to be displayed as a synthetic image on the display 54. For example, the display control function 170 reads out the synthetic image data of the object P stored in the image data memory circuitry 53 and causes the synthetic image to be displayed on the display 54.

(Synthetic Image Display Processing)

Subsequently, synthetic image display processing for changing a working angle in the X-ray diagnostic imaging apparatus 10 of the first embodiment will be described by using a flowchart in FIG. 4 by referring to FIGS. 1 to 3.

Figure 4:
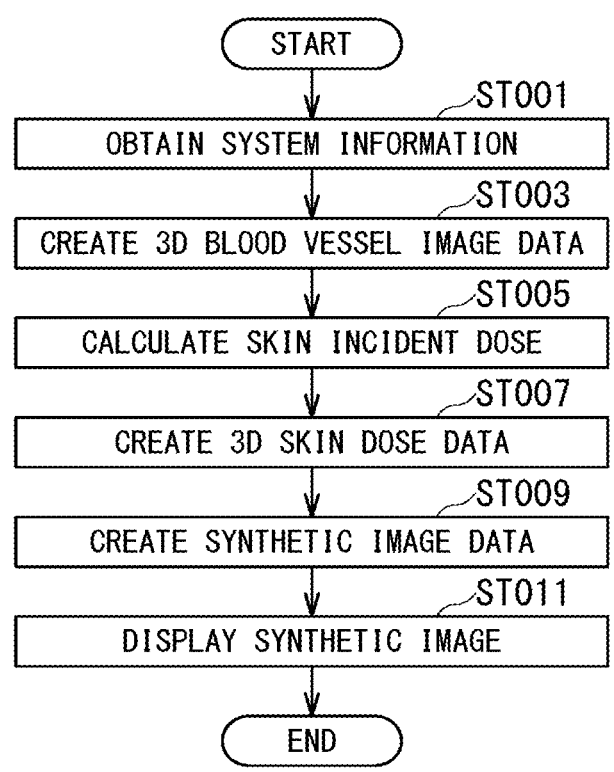
FIG. 4 is a flowchart illustrating synthetic image display processing in which the X-ray diagnostic imaging apparatus of the first embodiment displays a synthetic image of 3D blood vessel image data and 3D skin dose data.

FIG. 4 is a flowchart illustrating the synthetic image display processing in which the X-ray diagnostic imaging apparatus 10 of the first embodiment displays the synthetic image of the 3D blood vessel image data and the 3D skin dose data.

First, the X-ray diagnostic imaging apparatus 10 obtains system information by an operation of an operator through the input controller 44 prior to X-ray photography or X-ray therapy (Step ST001). For example, when the X-ray diagnostic imaging apparatus 10 receives an input of synthesizing the 3D blood vessel image data and the 3D skin dose data from the input controller 44, the processing circuitry 41 obtains the system information required for the synthetic image display from the controller 30 by the synthetic display information obtaining function 120. The processing circuitry 41 supplies the obtained system information to the blood vessel image creating function 110 or the synthetic display information obtaining function 120.

Subsequently, the X-ray diagnostic imaging apparatus 10 creates the 3D blood vessel image data of the object P by the operation of the operator through the input controller 44 (Step ST003). For example, the X-ray diagnostic imaging apparatus 10 may create photographed image data at photographing from the projection data in the rotating photographing and create the 3D blood vessel image data or may create the 3D blood vessel image data from the image data photographed in advance.

Moreover, the X-ray diagnostic imaging apparatus 10 calculates the skin incident dose during an operation on the object P at all times from start of the operation by the operator and accumulates the skin incident doses to the object P during photographing (Step ST005). For example, the X-ray diagnostic imaging apparatus 10 obtains the angle of the C-arm 26, the SID, the human body model showing the physical characteristics of the object P, the X-ray irradiation information and the like by the synthetic display information obtaining function 120 and calculates the accumulative exposure doses and exposure regions to the object P during the photographing since the operation was started by the skin dose calculating function 130.

When the skin incident dose is calculated at Step ST005, the X-ray diagnostic imaging apparatus 10 creates 3D skin dose data displaying the skin incident dose at the body surface position of the human body model showing the object P (Step ST007). For example, the X-ray diagnostic imaging apparatus 10 obtains the human body model showing the physical characteristics of the object P from the human body model database 150 and creates the 3D skin dose data displaying the skin incident dose on the human body model by the skin incident dose information creating function 140.

Figure 5A:
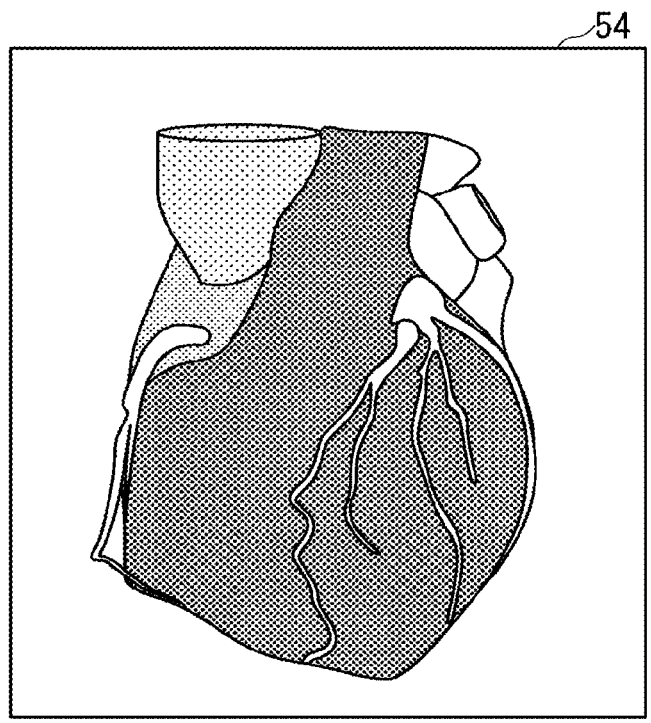
FIG. 5A is an explanatory view illustrating an image of the 3D blood vessel image data generated at Step ST003.
Figure 5B:
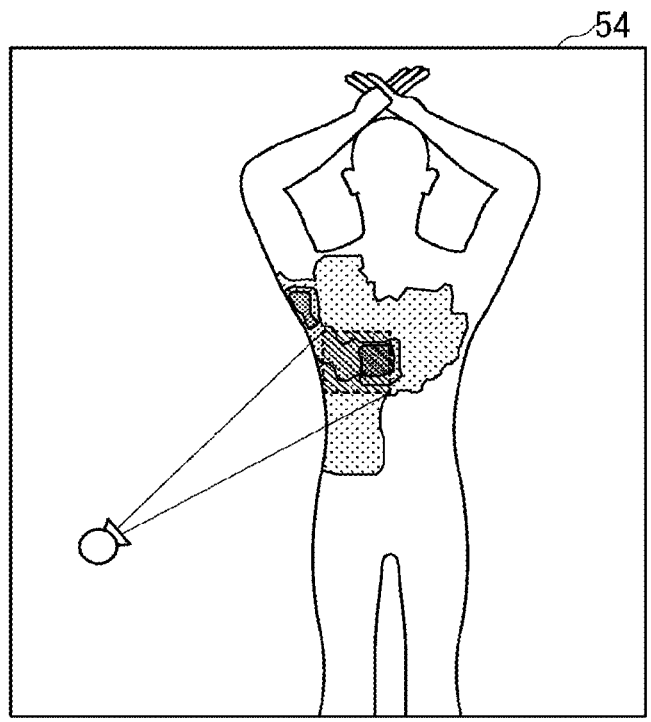
FIG. 5B is an explanatory view illustrating an image of the 3D skin dose data generated at Step ST007.

FIG. 5A is an explanatory view illustrating an image of the 3D blood vessel image data created at Step ST003. FIG. 5B is an explanatory view illustrating an image of the 3D skin dose data created at Step ST007.

In FIG. 5A, an image of the 3D blood vessel image data created at Step ST003 is shown. In FIG. 5B, an image of the 3D skin dose data created at Step ST007 is shown.

Subsequently, the X-ray diagnostic imaging apparatus 10 superposes the 3D blood vessel image data created at Step ST003 and the 3D skin dose data created at Step ST007 and creates the synthetic image data (Step ST009). For example, the X-ray diagnostic imaging apparatus 10 obtains the 3D blood vessel image data from the blood vessel image creating function 110 and obtains the 3D skin dose data from the skin incident dose information creating function 140 by the synthetic image creating function 160. The processing circuitry 41 synthesizes the 3D blood vessel image data and the 3D skin dose data by the synthetic image creating function 160 and creates the synthetic image data.

At Step ST009, when the 3D blood vessel image data and the 3D skin dose data are to be synthesized, in this embodiment, the following five functions are provided as arbitrary constituent elements.

A first function is a function of alignment. For example, the synthetic image creating function 160 of the X-ray diagnostic imaging apparatus 10 is provided with a function of executing alignment between the 3D blood vessel image data and the 3D skin dose data from a height, a weight, a body type and the like of the object P in the system information obtained by the synthetic display information obtaining function 120. In the first embodiment, an example in which the 3D skin dose data is aligned with a position of the 3D blood vessel image data will be described, but this is not limiting. For example, the 3D blood vessel image data may be aligned with the position of the 3D skin dose data.

A second function is a function of specifying a display region. For example, the synthetic image creating function 160 is provided with a function of superposing an X-ray image data display region showing a range for irradiating the X-ray to the object P further on the synthetic image data and displaying it on the display 54 when the 3D blood vessel image data and the 3D skin dose data are superposed with each other. In this case, the processing circuitry 41 can cause the X-ray image data display region to be displayed on the synthetic image by the synthetic image creating function 160.

A third function is a function of reversing the 3D skin dose data. For example, the processing circuitry 41 is provided with a function of switching right and left values of dose shown by the 3D skin dose data when the 3D blood vessel image data and the 3D skin dose data are to be superposed with each other by the synthetic image creating function 160. In this embodiment, the 3D blood vessel image data is assumed to be an image when seen from a front of the object P, and the 3D skin dose data is assumed to be an image when the X-ray is irradiated from behind the object P as an example.

For example, when display of the X-ray image such as transparency is examined, a projected image is a projected image in a direction in which the object P is seen from the detector 28 side. Thus, when skin dose information is assumed to be aligned with the projected image seen from the detector 28 side, the processing circuitry 41 switches the right and left values of the dose shown by the 3D skin dose data, and the 3D skin dose data is reversed in order to match appearances of the images of the 3D blood vessel image data and the 3D skin dose data. A display method is an example and is not limiting.

A fourth function is a function of enlarging the 3D skin dose data. For example, the processing circuitry 41 is provided with a function of executing enlargement processing to the 3D skin dose data and matching a size of a region with the 3D blood vessel image data by the synthetic image creating function 160. The synthetic image creating function 160 is also provided with processing of reduction, not limited to the enlargement processing.

Figure 6A:
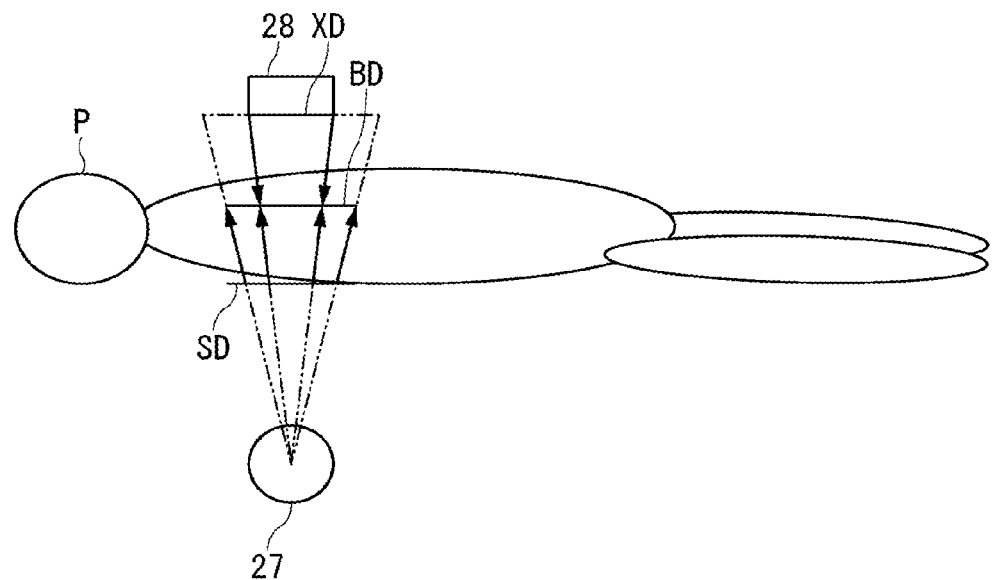
FIG. 6A is a conceptual diagram when the synthetic image data is generated in a synthetic image creating function of the X-ray diagnostic imaging apparatus according to the first embodiment.
Figure 6B:
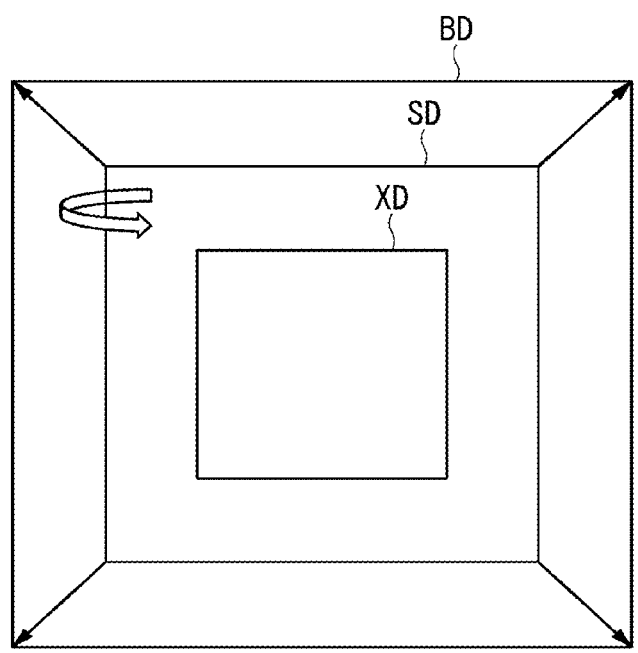
FIG. 6B is a conceptual diagram when the synthetic image data is generated in the synthetic image creating function of the X-ray diagnostic imaging apparatus according to the first embodiment.

FIGS. 6A and 6B are conceptual diagrams when the synthetic image data is to be created in the synthetic image creating function 160 of the X-ray diagnostic imaging apparatus 10 according to the first embodiment.

In FIG. 6A, a concept of creating the synthetic image data in the object P (or the human body model) is illustrated, while in FIG. 6B, in order to match the positions and the sizes of the 3D skin dose data and the 3D blood vessel image data with each other, a concept in which right and left values of the dose of the 3D skin dose data are switched and enlarged and synthesized with the 3D blood vessel image data is illustrated.

For example, in FIG. 6A, the X-ray is irradiated to the object P (or the human body model) by the X-ray irradiating device 27 and the detector 28, and the processing circuitry 41 switches the right and left values of the dose of the 3D skin dose data SD by the synthetic image creating function 160 as illustrated in FIG. 6B. Then, the processing circuitry 41 enlarges the 3D skin dose data SD by the synthetic image creating function 160 and matches a size of a region with a position corresponding to the 3D blood vessel image data BD in the object P and creates the synthetic image data.

The processing circuitry 41 can superpose an X-ray image data display region XD on the synthetic image data of the 3D blood vessel image data BD and the 3D skin dose data SD by the synthetic image creating function 160 and cause the X-ray image data display region XD to be displayed on the synthetic image. Processing of superposing the X-ray image data display region XD is not limited to the superposing by the synthetic image creating function 160, but the X-ray image data display region XD may be superposed by the display control function 170, for example.

The X-ray diagnostic imaging apparatus 10 receives an input of a mouse constituting the input controller 44, and by selecting the synthetic image by the mouse and by performing a rotating operation of the mouse in a direction in which the synthetic image is to be seen, the synthetic image can be rotated in accordance with the operation, for example.

Here, a fifth function is a highlighting function for making highlighted display in accordance with an operation situation of the synthetic image. For example, as the highlighting function, if the 3D blood vessel image is being rotated by the synthetic image creating function 160, the processing circuitry 41 highlights the 3D blood vessel image, while if the 3D blood vessel image is not being rotated (stopped), the processing circuitry 41 highlights information shown by the 3D skin dose data.

Figure 7:
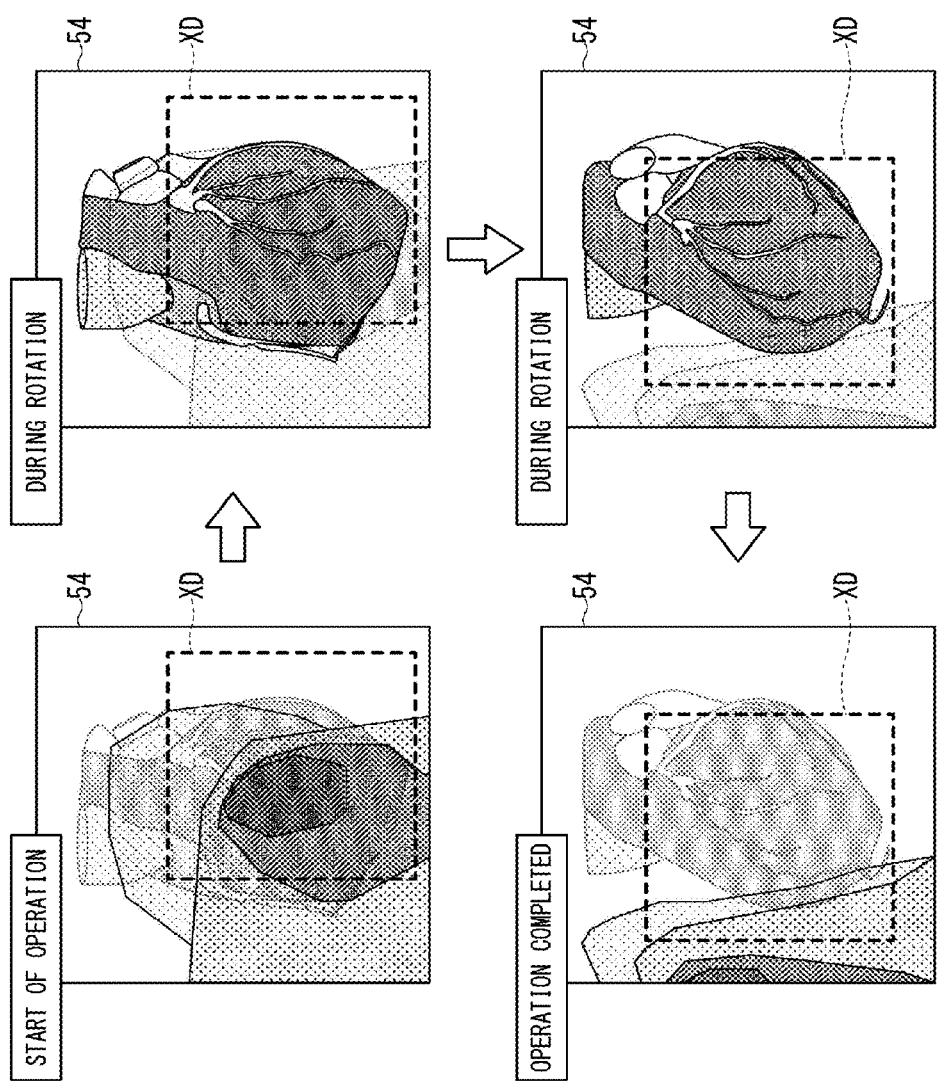
FIG. 7 is an explanatory view illustrating a display form of highlighted display when processing circuitry rotates the synthetic image by the synthetic image creating function of the X-ray diagnostic imaging apparatus according to the first embodiment.

FIG. 7 is an explanatory view illustrating a display form of highlighting when the processing circuitry 41 rotates the synthetic image by the synthetic image creating function 160 of the X-ray diagnostic imaging apparatus 10 according to the first embodiment.

As illustrated at start of an operation in FIG. 7, the processing circuitry 41 highlights an image shown by the 3D skin dose data more than the 3D blood vessel image before the synthetic image (that is, the three-dimensional blood vessel image) is rotated by the mouse by the synthetic image creating function 160. On the other hand, as illustrated during rotation in FIG. 7, if the synthetic image (that is, the three-dimensional blood vessel image) is being rotated by using the mouse, the processing circuitry 41 highlights the 3D blood vessel image more than the image shown by the 3D skin dose data by the synthetic image creating function 160. At the end of the operation in FIG. 7, a case in which the processing of rotating/operating the synthetic image (that is, the three-dimensional blood vessel image) is completed is illustrated, and the processing circuitry 41 highlights the image shown by the 3D skin dose data more than the 3D blood vessel image by the synthetic image creating function 160.

From the start of the operation to the completion of the operation in FIG. 7, a region surrounded by a broken line indicates the X-ray image data display region XD.

The X-ray diagnostic imaging apparatus 10 causes the synthetic image data created at Step ST009 to be displayed as a synthetic image on the display 54 (Step ST011).

As described above, when the synthetic image data is created by the synthetic image creating function 160, the processing circuitry 41 causes the display 54 to display the synthetic image. Then, the X-ray diagnostic imaging apparatus 10 of the first embodiment ends the synthetic image display processing.

As described above, the X-ray diagnostic imaging apparatus 10 according to the first embodiment can create the synthetic image data of the 3D skin dose data and the 3D blood vessel image data by the synthetic image creating function 160. Moreover, the X-ray diagnostic imaging apparatus 10 receives the operation input of the mouse constituting the input controller 44, and if the synthetic image (a 3D blood vessel image, for example) is being rotated, the X-ray diagnostic imaging apparatus 10 highlights the 3D blood vessel image, while if the synthetic image (a 3D blood vessel image, for example) is not being rotated (stopped), the X-ray diagnostic imaging apparatus 10 can highlight the image shown by the 3D skin dose data.

According to the X-ray diagnostic imaging apparatus 10 according to the first embodiment, since the operator can check how the 3D blood vessel image is seen if the synthetic image (a 3D blood vessel image, for example) is being rotated and can check an exposure situation by the image of the 3D skin dose data if the synthetic image (a 3D blood vessel image, for example) is stopped, the operator can easily determine a working angle indicating an appropriate arm position considering the skin incident dose.

To the 3D skin dose data, three-dimensional data based on a position of the 3D blood vessel image can be applied instead of the three-dimensional data based on a position on the body surface. Thus, the operator can apply the three-dimensional data at a position to be desirably checked to this embodiment. Moreover, as another optional constitution, it may be so constituted that synthetic display based on the position on the body surface and the display of the synthetic image based on the position of the 3D blood vessel image are selectively switched.

In the X-ray diagnostic imaging apparatus 10 according to the first embodiment, after the 3D blood vessel image data and the 3D skin dose data are aligned with each other, they are superposed and the synthetic image data is created. Thus, alignment from the body surface to the blood vessel image can be made with high accuracy, and accuracy of the exposure dose and the exposure region can be improved.

Moreover, in the X-ray diagnostic imaging apparatus 10 according to the first embodiment, the synthetic image is displayed with the information of the 3D skin dose data superposed/displayed on the 3D blood vessel image and thus, the operator can instinctively and easily recognize the exposure dose or an exposure situation of the exposure region.

In this embodiment, alignment of three-dimensional data of the 3D blood vessel image data and the 3D skin dose data is executed and the synthetic image data is created, but this is not limiting.

For example, the processing circuitry 41 creates the three-dimensional image showing the blood vessel image from the projection data obtained by photographing by the blood vessel image creating function 110 and creates dose data showing information of skin incident dose to the object P by the skin incident dose information creating function 140. Then, the processing circuitry 41 may be in such a form that the image shown by the dose data is superposed on the three-dimensional image showing this blood vessel image by the synthetic image creating function 160 and the synthetic image is created.

Second Embodiment

In the first embodiment, the X-ray diagnostic imaging apparatus 10 is constituted such that the synthetic image data of the 3D skin dose data and the 3D blood vessel image data is displayed as the synthetic image on the display 54. In a second embodiment, with regard to the X-ray image data display region in the 3D skin dose data or the 3D blood vessel image data, a region corresponding to each other is displayed by the display control function 170 of the X-ray diagnostic imaging apparatus 10.

Figure 8:
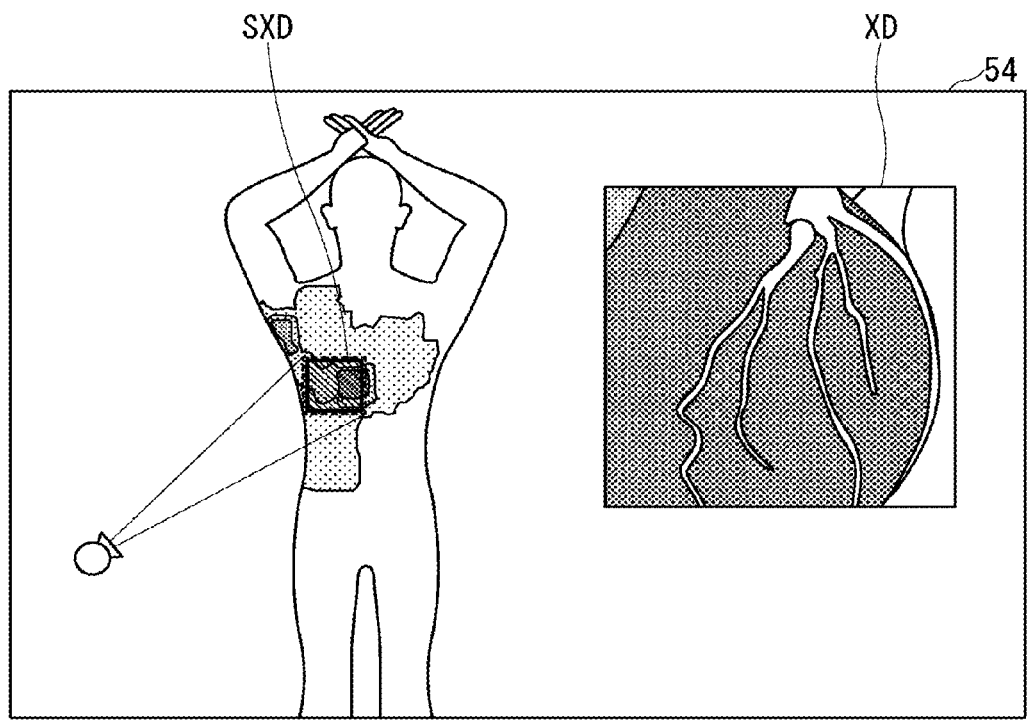
FIG. 8 is an explanatory view when the 3D blood vessel image corresponding to an X-ray image data display region is displayed in an image indicated by the 3D skin dose data on a display as an example of the X-ray diagnostic imaging apparatus according to a second embodiment.

FIG. 8 is an explanatory view when the X-ray diagnostic imaging apparatus 10 according to the second embodiment causes a 3D blood vessel image corresponding to an X-ray image data display region SXD in the image shown by the 3D skin dose data to be displayed on the display 54 as an example.

As illustrated in FIG. 8, the X-ray diagnostic imaging apparatus 10 according to the second embodiment causes a 3D blood vessel image corresponding to the X-ray image data display region SXD to be displayed on the display 54 by the display control function 170 as a 3D blood vessel image of the x-ray image data display region XD as an example. In this case, the processing circuitry 41 creates the 3D blood vessel image data in accordance with the X-ray image data display region XD of the 3D blood vessel image data by the synthetic image creating function 160.

The X-ray diagnostic imaging apparatus 10 according to the second embodiment may cause the X-ray image data display region XD of the 3D blood vessel image to be pop-up-displayed in a vicinity of the X-ray image data display region SXD of the image shown by the 3D skin dose data by the display control function 170 based on setting by the operator. In this case, the operator may set a display size of the X-ray image data display region XD in advance and execute enlargement processing or reduction processing to the 3D blood vessel image data.

The X-ray diagnostic imaging apparatus 10 may cause the image shown by the 3D skin dose data of the corresponding region for the X-ray image data display region to be displayed by the display control function 170 with regard to the 3D blood vessel image data. In this case, the synthetic image creating function 160 preferably switches the right and left values of the dose shown by the 3D skin dose data.

If the working angle is to be changed, it is preferable that the operator sees the image of the 3D blood vessel image data for making determination, and thus, the 3D blood vessel image in the X-ray image data display region SXD as described above is preferably displayed.

For example, if the operator performs the rotating operation to the image shown by the 3D skin dose data or the 3D blood vessel image by using the mouse, it may be so constituted that the 3D blood vessel image corresponding to the X-ray image data display region SXD is interlocked with the rotating operation and the corresponding 3D blood vessel image is rotated/displayed by the operation.

Third Embodiment

In the first embodiment and the second embodiment, the synthetic image (that is, the 3D blood vessel image) is rotated/displayed by using the mouse, but this is not limiting.

For example, the X-ray diagnostic imaging apparatus 10 according to a third embodiment creates one or a plurality of pieces of synthetic image data at an interval of a predetermined working angle within a range capable of irradiating the object P with the X-ray by the synthetic image creating function 160. The processing circuitry 41 causes one or a plurality of synthetic images shown by the one or the plurality of pieces of synthetic image data to be displayed on the display 54 by the display control function 170. The X-ray diagnostic imaging apparatus 10 receives selection of one synthetic image from the one or the plurality of synthetic images and causes the synthetic image to be displayed on the display 54 at the working angle corresponding to the selected synthetic image.

As described above, in the third embodiment, as one method for determining the working angle, one or a plurality of pieces of synthetic image data is created at a predetermined angle with respect to one or a plurality of directions, for example. In this case, the operator can select a candidate of the working angle from the one or the plurality of synthetic images corresponding to the one or the plurality of pieces of synthetic image data without rotating/displaying the synthetic image by the mouse.

Fourth Embodiment

In a fourth embodiment, a dose map showing a maximum skin incident dose or an average skin incident dose is created on the basis of the skin incident dose, and an angle of the working angle is selected or determined.

For example, in the X-ray diagnostic imaging apparatus 10 according to the fourth embodiment, the dose map showing the maximum skin incident dose or the average skin incident dose in the X-ray image data display region XD is created on the basis of the skin incident dose within a range capable of irradiating the object P with the X-ray by the skin incident dose information creating function 140.

The processing circuitry 41 associates the dose map with the 3D blood vessel image data by the display control function 170 and causes the 3D blood vessel image (three-dimensional image) corresponding to a position shown by the dose map or a position of the dose map corresponding to an irradiation angle of the 3D blood vessel image to be displayed.

Figure 9A:
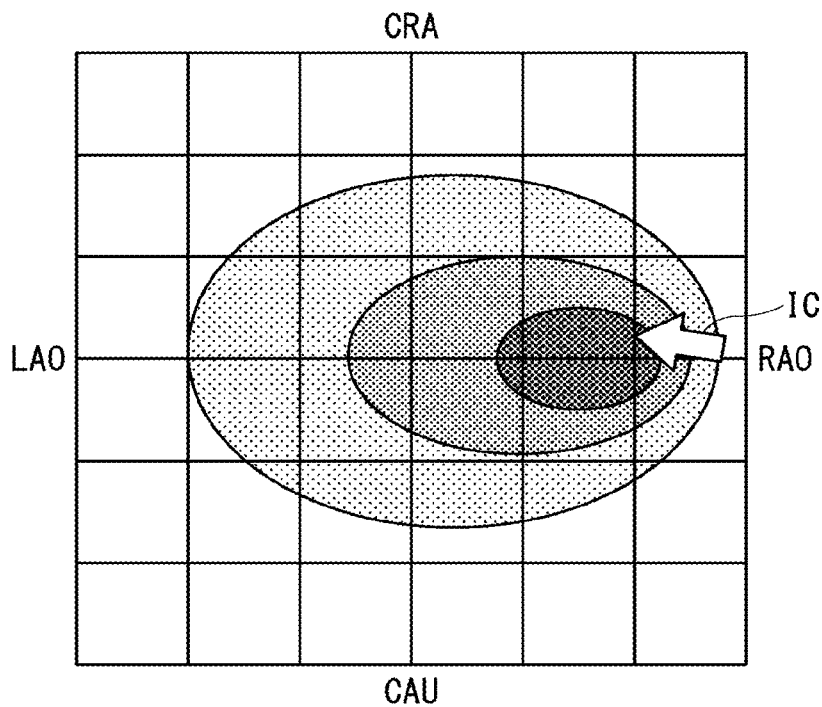
FIG. 9A is an explanatory view when a dose map showing a maximum skin incident dose in the X-ray image data display region is displayed on the display by an X-ray diagnostic imaging apparatus according to a fourth embodiment.
Figure 9B:
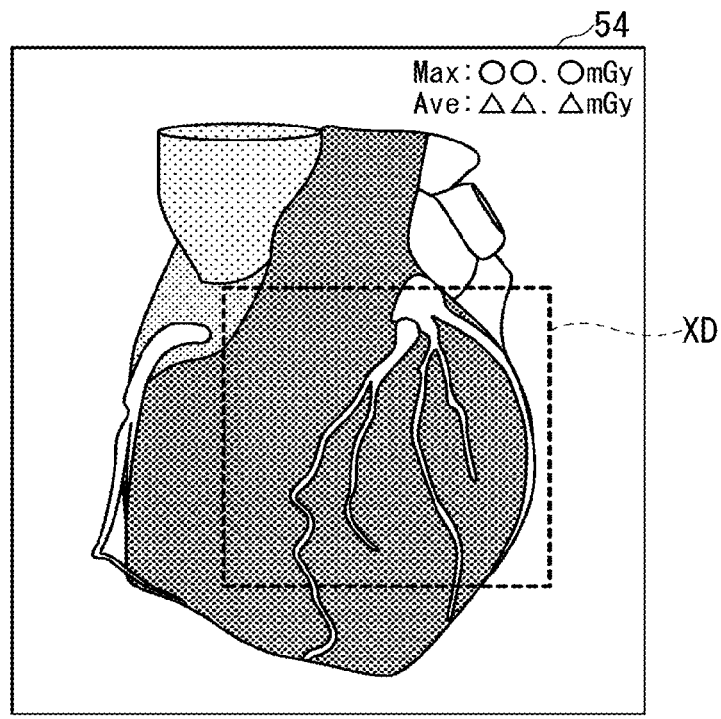
FIG. 9B is an explanatory view when a 3D blood vessel image at an angle of a working angle corresponding to the dose map is displayed on the display by the X-ray diagnostic imaging apparatus according to the fourth embodiment.

FIG. 9A is an explanatory view when the X-ray diagnostic imaging apparatus 10 according to the fourth embodiment causes the dose map showing the maximum skin incident dose in the X-ray image data display region XD to be displayed on the display 54. FIG. 9B is an explanatory view when the X-ray diagnostic imaging apparatus 10 according to the fourth embodiment causes the 3D blood vessel image at an angle of the working angle corresponding to the dose map to be displayed on the display 54.

In FIG. 9A, the dose map showing the maximum skin incident dose is illustrated, and an icon IC indicates an angle of the working angle (position shown by the dose map) and the maximum skin incident dose at that angle. In FIG. 9B, the 3D blood vessel image at the angle of the working angle shown by the icon IC is illustrated.

In FIG. 9A, an angle given by rotating in a right-hand direction when a longitudinal direction (body axis direction) of the object P is used as an axis is referred to as RAO (Right Anterior Oblique). An angle given by rotating in a left-hand direction when the longitudinal direction (body axis direction) of the object P is used as an axis is referred to as LAO (Left Anterior Oblique). An angle given by rotating in a head part direction when a transverse direction of the object P is used as an axis is referred to as CRA (Cranial). An angle given by rotating in a foot part direction when the transverse direction of the object P is used as an axis is referred to as CAU (Caudal).

In the fourth embodiment, the X-ray diagnostic imaging apparatus 10 specifies the angle of the working angle using RAO, LAO, CRA, and CAU.

In FIGS. 9A and 9B, by operating the icon IC in FIG. 9A by the mouse, the 3D blood vessel image in FIG. 9B changes in accordance with a change of the angle of the working angle with the operation of the mouse. That is, when the operator moves the icon IC by the operation of the mouse, the X-ray diagnostic imaging apparatus 10 changes the angle of the working angle and changes a position or a direction of the 3D blood vessel image in FIG. 9B without directly changing the angle of the C-arm 26. If the operator operates the 3D blood vessel image in FIG. 9B with the mouse, the X-ray diagnostic imaging apparatus 10 moves the icon IC indicating the angle of the working angle in FIG. 9A with the change of the 3D blood vessel image without directly changing the position of the corresponding C-arm 26.

In the fourth embodiment, the X-ray diagnostic imaging apparatus 10 can cause the angle of the working angle shown by the icon IC and the maximum skin dose at the angle and the 3D blood vessel image to be displayed on the display 54 before operating the C-arm 26 and thus, the operator can select or change the optimal working angle before operating the C-arm 26.

The X-ray diagnostic imaging apparatus 10 is so constituted that the icon IC and the C-arm 26 are interlocked and the C-arm 26 is moved to the angle of the working angle determined by the operator when the working angle is determined by the icon IC. For example, when the operator makes a decision on the angle of the working angle selected by the operation of the icon IC by the operator, the angle of the C-arm 26 is changed to the determined angle of the working angle.

As a result, in the fourth embodiment, the operator can select or change the working angle by referring to the dose map showing the maximum skin incident dose or the average skin incident dose.

In the fourth embodiment, as illustrated in upper right in FIG. 9B, numeral values of the maximum skin incident dose (Max: xx.x mGy) or the average skin incident dose (Ave: yy.y mGy) in the X-ray image data display region XD may be displayed, respectively.

Fifth Embodiment

In the fourth embodiment, the X-ray diagnostic imaging apparatus 10 creates the dose map showing the maximum skin incident dose or the average skin incident dose so that the operator can select or change the angle of the working angle by referring to the dose map. In a fifth embodiment, a dose map showing an estimated skin incident dose is created so that the angle of the working angle is selected or changed.

For example, in the fifth embodiment, an exposure situation assumed when the angle of the working angle is changed is estimated from a current exposure situation, and appearance of the 3D blood vessel image assumed after the working angle is changed is displayed. In this case, the X-ray diagnostic imaging apparatus 10 is not interlocked with the icon IC and with the C-arm 26 but displays the 3D blood vessel image when the assumed angle of the working angle is changed on the display 54.

That is, the X-ray diagnostic imaging apparatus 10 according to the fifth embodiment creates the estimated dose map showing the estimated skin incident dose in the X-ray image data display region XD within a range capable of irradiating the object P with the X-ray by the skin incident dose information creating function 140.

The processing circuitry 41 associates the estimated dose map with the 3D blood vessel image and causes the 3D blood vessel image (three-dimensional image) corresponding to a position shown by the estimated dose map or a position of the estimated dose map corresponding to an irradiation angle of the 3D blood vessel image to be displayed by the display control function 170.

Figure 10A:
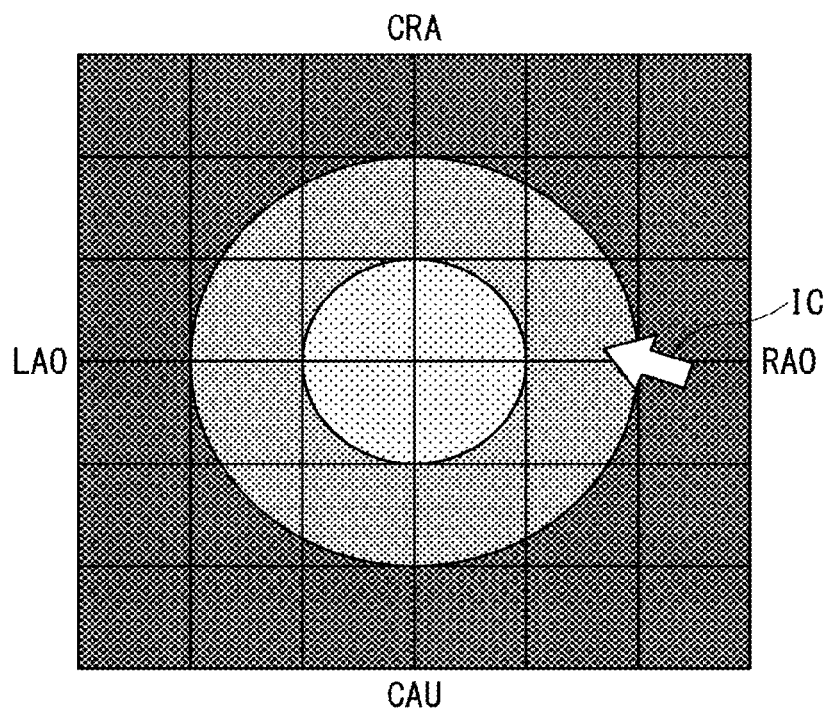
FIG. 10A is an explanatory view when an estimated dose map in the X-ray image data display region is displayed on the display by the X-ray diagnostic imaging apparatus according to a fifth embodiment.
Figure 10B:
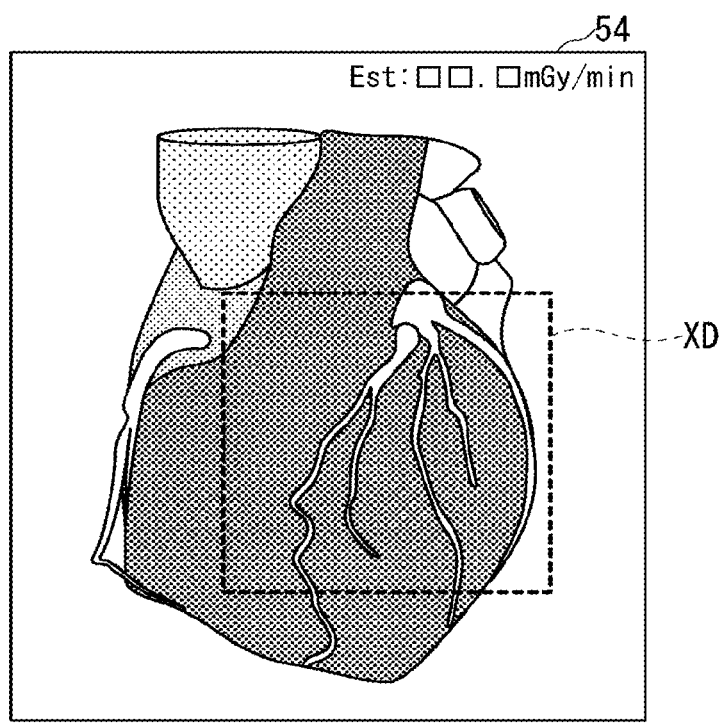
FIG. 10B is an explanatory view when the 3D blood vessel image at the angle of the working angle corresponding to the estimated dose map is displayed on the display by the X-ray diagnostic imaging apparatus according to the fifth embodiment.

FIG. 10A is an explanatory view when the X-ray diagnostic imaging apparatus 10 according to the fifth embodiment displays the estimated dose map in the X-ray image data display region XD on the display 54. FIG. 10B is an explanatory view when the X-ray diagnostic imaging apparatus 10 according to the fifth embodiment displays the 3D blood vessel image at the angle of the working angle corresponding to the estimated dose map on the display 54.

In FIG. 10A, the estimated dose map showing the estimated skin incident dose is illustrated, and the icon IC indicates the angle of the working angle (position shown by the dose map) and the estimated skin incident dose at that angle. In FIG. 10B, the 3D blood vessel image at the angle of the working angle shown by the icon IC is illustrated.

In the fifth embodiment, in a method of specifying the working angle, the angle of the working angle is assumed to be specified by using RAO, LAO, CRA, and CAU similarly to the fourth embodiment.

In FIGS. 10A and 10B, by operating the icon IC in FIG. 10A by the mouse, the 3D blood vessel image in FIG. 10B changes in accordance with a change of the angle of the working angle with the operation of the mouse. That is, when the operator moves the icon IC by the operation of the mouse, the X-ray diagnostic imaging apparatus 10 changes the angle of the working angle and changes a position or a direction of the 3D blood vessel image in FIG. 10B without directly changing the angle of the C-arm 26. If the operator operates the 3D blood vessel image in FIG. 10B with the mouse, the X-ray diagnostic imaging apparatus 10 moves the icon IC indicating the angle of the working angle in FIG. 10A with the change of the 3D blood vessel image without directly changing the position of the corresponding C-arm 26.

As described above, in the case of the fifth embodiment, since the exposure situation of the 3D blood vessel image assumed when the angle of the working angle is changed from the current exposure situation can be displayed, the operator can check the assumed exposure situation and appearance of the 3D blood vessel image after the angle of the working angle is changed.

In the fifth embodiment, as illustrated in FIG. 10B, numeral values of the estimated skin incident dose (Est: zz.z mGy/min) of the X-ray image data display region XD may be displayed.

A term "processor" used in the aforementioned description refers to a circuitry such as a dedicated or general-purpose CPU (Central Processing Unit), an ASIC (Application Specific Integrated Circuit), a programmable logic device (a simple programmable logic device: SPLD, for example), a CPLD (Complex Programmable Logic Device), and an FPGA (Field Programmable Gate Array) and the like. In FIG. 1, an example in which the number of processors used in the processing circuitry 41 is one is illustrated, but the number of processors may be two or more.

The processor used in the processing circuitry 41 realizes each function by reading out and executing programs stored in a memory circuitry of the memory 42 or the HDD 43 or directly incorporated in a circuitry of the processor. If a plurality of the processors is provided, the memory 42 or the HDD 43 storing the programs may be provided individually for each processor or the memory 42 or the HDD 43 in FIG. 1 may store the program corresponding to a function of each processor.

Some embodiments of the present invention are described but these embodiments are presented as examples and are not intended to limit a scope of the invention. These embodiments can be executed in other various forms and are capable of various types of omission, replacement or changes within a range not departing from the gist of the invention. These embodiments and their variations are included in the scope and the gist of the invention and also included in the invention described in claims and their equivalents.

What is claimed is:

1. A medical image processing apparatus comprising:
a processing circuitry configured to:
calculate an incident dose on a body surface of an object,
superpose information based on the calculated incident dose, on three-dimensional original image data including an internal structure relating to the object so as to correspond to each position of the body surface of the object, thereby creating three-dimensional synthetic image data,
cause a synthetic image, based on the three-dimensional synthetic image data, to be displayed on a display,
receive an input operation to rotate the three-dimensional synthetic image data, and
cause a synthetic image, based on rotated three-dimensional synthetic image data, to be displayed on the display.

2. The apparatus according to claim 1, wherein the three-dimensional original image data is medical image data obtained by imaging the object.

3. The apparatus according to claim 1, wherein the three-dimensional original image data is medical image data including a blood vessel of the object as the internal structure.

4. The apparatus according to claim 1, wherein the processing circuitry is configured to calculate a skin exposure dose of the object as the incident dose.

5. The apparatus according to claim 1, wherein the processing circuitry is configured to create and display, while the three-dimensional synthetic image data is rotating, synthetic images which highlight the three-dimensional original image data, and to create and display, while the three-dimensional synthetic image data is not rotating, synthetic images which highlight the information based on the incident dose.

6. A medical image processing apparatus comprising:
processing circuitry configured to:
calculate an incident dose to an object,
superpose information, based on the calculated incident dose, on three-dimensional original image data including an internal structure relating to the object, and
cause a synthetic image, based on the three-dimensional synthetic image data, to be displayed on a display, wherein
the processing circuitry is configured to create and display, while the three-dimensional synthetic image data is rotating, synthetic images which highlight the three-dimensional original image data, and create and display, while the three-dimensional synthetic image data is not rotating, synthetic images which highlight the information based on the incident dose.

7. The apparatus according to claim 6, wherein the three-dimensional original image data is medical image data obtained by imaging the object.

8. The apparatus according to claim 6, wherein the three-dimensional original image data is medical image data including a blood vessel of the object as the internal structure.

9. The apparatus according to claim 6, wherein the processing circuitry is configured to superpose information, based on the incident dose, on the three-dimensional original image data so as to correspond to each position of the body surface of the object, thereby creating the three-dimensional synthetic image data.

10. The apparatus according to claim 6, wherein the processing circuitry is configured to:
create first three-dimensional data as the three-dimensional original image data,
create second three-dimensional data showing information based on the incident dose at a body surface position of a human body model showing the object, and
create the three-dimensional synthetic image data in which the first three-dimensional data and the second three-dimensional data are superposed.

11. The apparatus according to claim 10, wherein the processing circuitry is configured to superpose the first three-dimensional data and the second three-dimensional data by horizontal-mirror-reversing dose values shown in the second three-dimensional data when the first three-dimensional data and the second three-dimensional data are to be superposed.

12. The apparatus according to claim 10, wherein the processing circuitry is configured to superpose the first three-dimensional data and the second three-dimensional data by executing enlargement processing to the second three-dimensional data when the first three-dimensional data and the second three-dimensional data are to be superposed.

13. The apparatus according to claim 10, wherein the processing circuitry is configured to further superpose an X-ray image data display region showing a range of irradiation of an X-ray to the object on the three-dimensional synthetic image data.

14. The apparatus according to claim 13, wherein
the processing circuitry is configured to cause mutually corresponding regions of the X-ray image data display region in the first three-dimensional data or the second-three-dimensional data to be displayed on the display.

15. The apparatus according to claim 10, wherein the processing circuitry is configured to:
create one or a plurality of the three-dimensional synthetic image data at a predetermined angular interval in a range where the X-ray is irradiated to the object,
cause the one or a plurality of the synthetic images, based on the one or plurality of three-dimensional synthetic image data, to be displayed on the display, and
cause, when one synthetic image from the one or plurality of synthetic image data is selected, the selected synthetic image to be displayed on the display at an irradiation angle corresponding to the selected synthetic image.

16. The apparatus according to claim 10, wherein the processing circuitry is configured to:
create a dose map showing a maximum incident dose or an average incident dose in an X-ray image data display region showing a range of irradiation of the X-ray to the object on the basis of the incident dose in a range where the X-ray is irradiated to the object,
associate a three-dimensional image obtained by photographing the object with the dose map, and
cause the three-dimensional image corresponding to a position shown by the dose map or a position of the dose map corresponding to an irradiation angle of the three-dimensional image to be displayed.

17. The apparatus according to claim 10, wherein the processing circuitry is configured to:
create an estimated dose map showing an estimated incident dose in an X-ray image data display region showing a range of irradiation of the X-ray to the object in a range where the X-ray is irradiated to the object,
associate a three-dimensional image obtained by photographing the object with the estimated dose map, and
cause the three-dimensional image corresponding to a position shown by the estimated dose map or a position of the estimated dose map corresponding to an irradiation angle of the three-dimensional image to be displayed.

18. The apparatus according to claim 10, wherein the three-dimensional original image data is medical image data including a blood vessel of the object as the internal structure.

19. An X-ray diagnostic imaging apparatus comprising:
an image generating apparatus configured to generate the three-dimensional original image data; and
the medical image processing apparatus according to claim 1.

20. An X-ray diagnostic imaging apparatus comprising:
an image generating apparatus configured to generate the three-dimensional original image data; and
the medical image processing apparatus according to claim 6.

* * * * *